United States Patent [19]

Alroy et al.

[11] Patent Number: 4,958,007

[45] Date of Patent: Sep. 18, 1990

[54] EXTRACTION OF HUMAN INTERLEUKIN-4- FROM BACTERIA

[75] Inventors: Yair Alroy, Parsippany; Paul Leibowitz, Hackensack, both of N.J.

[73] Assignee: Schering-Plough Corp., Kenilworth, N.J.

[21] Appl. No.: 194,799

[22] Filed: May 17, 1988

[51] Int. Cl.$^5$ .............................................. C07K 3/12
[52] U.S. Cl. ..................................... 530/351; 530/412; 530/418; 530/419; 530/420; 530/422; 530/423; 530/424; 530/427; 530/825; 435/69.5; 435/69.52; 435/71.1
[58] Field of Search ........ 530/351, 412, 418, 419–420, 530/422–424, 427, 825; 435/68, 69.5, 69.52, 71.1

[56] References Cited

U.S. PATENT DOCUMENTS

| | | | |
|---|---|---|---|
| 4,364,863 | 12/1982 | Leibowitz | 424/85.6 |
| 4,405,601 | 9/1983 | McEntire et al. | 424/95 |
| 4,675,387 | 6/1987 | Karant | 530/422 |

FOREIGN PATENT DOCUMENTS

| | | |
|---|---|---|
| 0173924 | 3/1986 | European Pat. Off. . |
| 0187386 | 7/1986 | European Pat. Off. . |
| 0230107 | 7/1987 | European Pat. Off. . |
| 0254399 | 1/1988 | European Pat. Off. . |
| 0291294 | 11/1988 | European Pat. Off. . |
| 3432196 | 6/1986 | Fed. Rep. of Germany . |
| WO87/00204 | 1/1987 | PCT Int'l Appl. . |
| 1432039 | 4/1976 | United Kingdom . |

OTHER PUBLICATIONS

Marston, *Biochem. J.*, 240, 1986, pp. 1–12.
Menge et al., *Develop. Biol. Std.*, 66, 1987, pp. 391–401.
European Journal of Biochemistry, vol. 173, No. 1, Apr. 1988, pp. 109–114.

*Primary Examiner*—Garnette Draper
*Attorney, Agent, or Firm*—Gerald S. Rosen; John J. Maitner

[57] ABSTRACT

A method is provided for extracting human interleukin-4 (IL-4) from IL-4 expressing bacterial cells. The method comprises treating the bacterial cells with a deactivating agent, disrupting the cell membrane and recovering the IL-4.

4 Claims, 1 Drawing Sheet

EXTRACTION OF HUMAN INTERLEUKIN-4 FROM BACTERIA

FIELD OF INVENTION

The invention relates generally to method for extracting proteins from bacteria, and more particularly, to methods for extracting human interleukin-4 expressed in bacteria.

BACKGROUND OF THE INVENTION

Interleukin-4 (IL-4) is a natural protein which has been discovered recently and which is believed to have a therapeutic potential against infection, cancer and autoimmune disease. Human IL-4 is reported by Yokota et al., Proc. Natl. Acad. Sci. USA, Vol. 83, pages 5894–5898 (1986). Mouse IL-4 is reported by Lee et al., Proc. Natl. Acad. Sci. USA, Vol. 83, pages 2061–2065 (1986), and Noma, et al., Nature, Vol. 319, pages 640–646 (1986).

Recombinant DNA techniques have been applied to the discovery of IL-4 as well as to the creation of bacteria which are capable of expressing IL-4. This has opened the way to large scale production of IL-4 which is required to investigate, develop and realize the therapeutic potential of this protein. However, clinical use of IL-4 requires high purity material that is not contaminated by cell constituents or cell debris of the IL-4-expressing cell. Accordingly, extraction of IL-4 from the cells of IL-4 expressing bacteria in sufficiently high purity and yield is required.

SUMMARY OF THE INVENTION

The present invention is based on the discovery that IL-4 can be extracted from IL-4-expressing bacteria by treating a suspension of IL-4 containing bacterial cells with an agent which deactivates (kills) the bacteria, disrupting the cells of the deactivated bacteria, and recovering the IL-4 from the disruptate. The method of this invention eliminates handling of live bacteria outside of the fermenter and allows recovery of the IL-4 in a manner which significantly reduces contamination by cultivation medium and cell constituents and permits efficient and economical purification afterwards.

DETAILED DESCRIPTION

Figure 1:
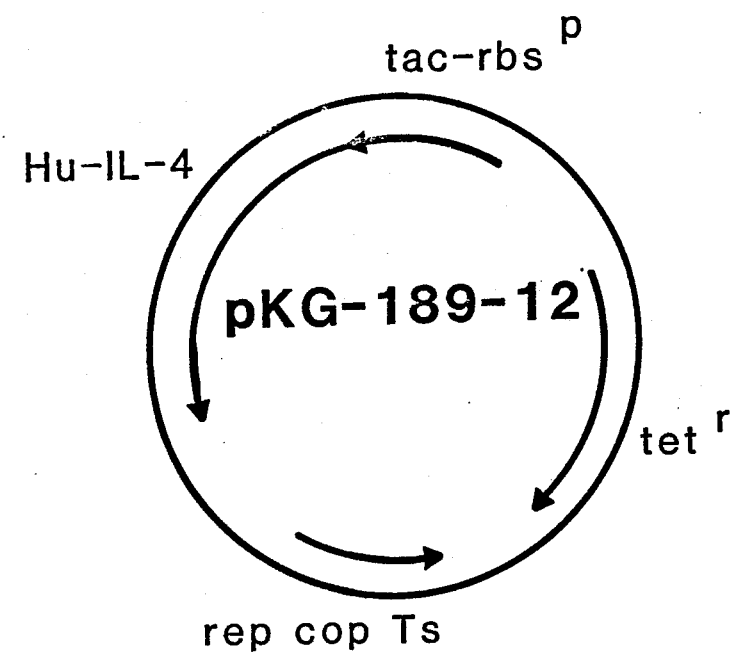
FIG. 1 is a construction map of plasmid pKG-189-12.

The present invention provides a method for extracting IL-4 from IL-4-expressing bacterial cells comprising:

(a) treating a suspension of IL-4 containing bacterial cells with an agent which deactivates the cells;
(b) disrupting the deactivated bacterial cells; and
(c) separating the IL-4 from the disruptate.

More specifically the method of this invention provides for extracting human IL-4 produced by genetically transformed bacteria, particularly E. coli. As used herein, the term "transformed bacteria" means bacteria that have been genetically engineered to produce human IL-4. Such genetic engineering usually entails the introduction of an expression vector into a bacterium. The expression vector is capable of autonomous replication and protein expression relative to genes in the bacterial genome. Construction of bacterial expression vectors is well known in the art, provided the nucleotide sequence encoding a desired protein is known or otherwise available. For example, DeBoer in U.S. Pat. No. 4,551,433 discloses promoters for use in bacterial expression vectors; Goeddel et al, in U.S. Pat. No. 4,601,980 and Riggs, in U.S. Pat. No. 4,431,739 disclose the production of mammalian proteins by E. coli expression systems; and Riggs (cited above), Ferretti et al (Proc. Natl. Acad. Sci., Vol. 83, pgs. 599–603, 1986), Sproat et al (Nucleic Acids Research, Vol. 13, pgs. 2959–2977, 1985) and Mullenbach et al (J. Biol. Chem., Vol. 261, pgs. 719–722, 1986) disclose how to construct synthetic genes for expression in bacteria. Accordingly, these references are incorporated by reference. The amino acid sequence of mature human IL-4 is disclosed by Yokota et al (Proc. Natl. Acad. Sci., Vol. 83. pp 5894–5898, 1986), and the cDNA encoding human IL-4 carried by the pcD vector described in Yokota et al. (cited above) is deposited with the American Type Culture Collection (ATCC), Rockville, Md., under accession number 53337. Many bacterial expression vectors and hosts are available commercially and through the ATCC. E. coli is the preferred bacterial host.

In carrying out the method of this invention, an agent which deactivates the cells is added to a suspension of IL-4-expressing cells. Agents which can be employed in this invention include benzoid hydrocarbons or acids. Examples of benzoid hydrocarbons which can be employed to deactivate the cells are toluene, the xylenes, p-cumene and the like.

If toluene is used to deactivate the cells, then sufficient toluene is added to provide a final concentration of about 0.1 to about 2% volume per volume. The preferred final concentration is about 1% volume per volume. After the toluene has been added, aeration is discontinued while agitation of the reaction is continued for about one hour. Aeration is then resumed and agitation of the reaction is continued until the level of toluene in the air leaving the culture falls below the low flammability limit.

If an acid is used to deactivate the cells, then sufficient acid is added to the suspension of IL-4-expressing cells to provide a pH of about 1.0 to about 3.0, preferably pH 2. Examples of suitable acids that can be utilized in this invention are hydrochloric acid, nitric acid, phosphoric acid and sulfuric acid. Phosphoric acid is the preferred acid.

In order to achieve complete cell deactivation and/or to improve the yield of extracted IL-4, it has been discovered that certain reagents, hereinafter referred to as "enhancing agents" may be added to the suspension of IL-4-expressing cells along with the acid. Examples of suitable enhancing agents include trichloroacetic acid or perchloric acid.

In one embodiment of the acidification step of the method of this invention, phosphoric acid is added to the suspension to lower the pH to about 4 to 5, preferably 4.5 and then trichloroacetic acid is added to lower the pH to 2.0.

After deactivating the cells with toluene or with acid, all subsequent steps of the method of this invention are carried out at a temperature of from about 0° C. to about 40° C., preferably 0°–4° C.

After the cells have been deactivated with toluene or with acid, the cells are prepared for disruption. This may be done simply by adjusting the pH of the deactivated cell suspension or alternatively, in order to achieve product concentration, by first separating the deactivated cells from the treated fermentation medium by centrifugation, filtration or other conventional means, then resuspending them in an acqueous buffer solution or in water occupying a fraction of the original fermentation volume, and finally adjusting the pH. Examples of buffers that may be used in resuspending the deactivated cells are sodium phosphate, potassium phosphate, tris(hydroxymethyl)aminoethane hydrochloride and the like. The preferred buffers are sodium phosphate and tris(hydroxymethyl)aminoethane hydrochloride. The pH of the deactivated cell suspension may be adjusted between 6.0 and 9.0 by addition of base. Examples of suitable bases that may be used in the pH adjustment step are sodium hydroxide, potassium hydroxide and the like.

After the deactivated cells have been prepared for disruption, the cells are disrupted. Conventional cell disruption techniques such as homogenization and sonication may be used in this step of the process. The preferred method of disruption is homogenization with a Manton-Gaulin homogenizer. The purpose of the disruption step is to break substantially all of the cells to a level which enables release of substantially all soluble cell components into the suspending medium. Although partial cell disruption may be achieved during the preceding deactivation step, a more complete cell disruption is achieved during this disruption step.

At the completion of the disruption step, the human IL-4 is found as a partially purified insoluble complex and is recovered by centrifugation, filtration or other conventional means.

The following example describes the invention in detail. It will be apparent to those skilled in the art that modification of materials and methods may be practiced without departing from the purpose and intent of this disclosure.

Example

The human IL-4 expression plasmid pKG-189-12 used in this example consists of about 3800 base pairs and includes the following sequences (see FIG. 1):
(a) The consensus promoter tac-rbs; Zurawski, et al., Journal of Immunology, Vol. 137, 3554–3360 (November 1986).
(b) The coding sequence for mature Hu-IL-4; Yokota, et al., Proc. Natl. Acad. Sci. USA, Vol. 83, 5894–5898 (August 1986). The 5' end of this coding sequence is fused with the 3' end of the tac promoter sequence.
(c) The temperature sensitive replicon, rep cop Ts, derived from the plasmid pVU208; Hakkaart, et al., Mol. Gen. Genet., Vol. 183, 326–332 (1981).
(d) The $tet^r$ gene for the expression of tetracycline resistance; Sutcliffe, Cold Spring Harbor Symposium Quantitative Biology 43, Part I, 77–90 (1979). Cold Spring Harbor Laboratory, Cold Spring Harbor, N.Y.

FERMENTATION

Add about 1 ml of an actively growing culture of E. coli 294 harboring the plasmid pKG-189-12 to about 10 liter of growth medium in a 16 liter fermenter. The growth medium consists of 30 g/l of casein hydrolysate, 20 g/l of yeast extract, 20 g/l of glycerol, 10 mg/l of tetracyline hydrochloride, 5 g/l of $KH_2PO_4$, 1 g/l $MgSO_4.7H_2O$, 0.1 ml/l of an antifoam agent and water.

Maintain the pH at 7 using 5 N NaOH and maintain the temperature at 30° C. while aerating and agitating the mixture until the cellular density of the culture reaches about 4 optical density units (660 μm, lightpath 1 cm). Raise the temperature to 37° C. and continue to aerate and agitate for 3 hours. Then reduce the temperature to 25° C. and proceed with the following extraction procedures (note: all subsequent centrifugations at Ca. 10,000 g for Ca. 15 min):

EXTRACTION PROCEDURE A

Add toluene to a final concentration of 1% volume per volume. Stop aeration and continue agitation for about 1 hour. Resume aeration and continue agitation until the level of toluene in the air leaving the culture falls below the low flammability limit. Centrifuge the detoluenized suspension and resuspend the pellet in sodium phosphate buffer 0.1 M pH 7.0 occupying a fraction of the original culture volume. The final biomass concentration of the resulting suspension is adjusted to correspond to about 30 optical density units of untreated culture. Disrupt the bacterial cells by passing the suspension through a Manton-Gaulin Laboratory Homogenizer (Model 15M) under ca. 8000 psi of pressure. Centrifuge the homogenate and discard the supernatant. The pellet contains recombinant human Interleukin-4.

EXTRACTION PROCEDURE B

Add a solution of 85% phosphoric acid to obtain pH 4.5. Add a solution of 50% trichloroacetic acid to pH 2 and agitate the acidified suspension for 1 hour. Carry out subsequent operations at a temperature of from 0° to 4°. Centrifuge the acid suspension. After centrifugation, discard the supernatant and resuspend the resulting bacterial pellet in sodium phosphate buffer 0.1 M, pH 8.5 occupying a fraction of the original culture volume. The pH of the resulting suspension is adjusted to 7.0–7.5 with 1 N sodium hydroxide. The final biomass concentration of the neutral suspension is adjusted to correspond to about 30 optical density units of untreated culture. Disrupt the bacterial cells by passing the neutral suspension through a Manton-Gaulin Laboratory Homogenizer (Model 15M) under ca. 8000 psi of pressure at 25° C. Centrifuge the homogenate and discard the supernatant. The pellet contains recombinant human Interleukin-4.

We claim:
1. A method of extracting insoluble interleukin-4 (IL-4) from IL-4 expressing bacterial cells comprising
   (a) treating a suspension of IL-4 containing bacterial cells with an agent selected from the group consisting of toluene or an acid selected from the group consisting of phosphoric acid, hydrochloric acid, nitric acid or sulfuric acid in the presence of an enhancing agent selected from the group consisting of trichloroacetic acid or perchloric acid to deactivate the bacterial cells;
   (b) disrupting the deactivated bacterial cells by mechanical means; and
   (c) separating the insoluble IL-4 from the disruptate.
2. The method of claim 1 wherein the bacterium is Escherichia coli.
3. The method of claim 1 wherein the interleukin-4 extracted is an insoluble pellet of human interleukin-4.
4. A method of extracting interleukin-4(IL-4) from IL-4-expressing cells comprising:
   (a) treating a suspension of IL-4 containing bacterial cells with toluene to deactivate the cells;
   (b) disrupting the deactivated bacterial cells;
   (c) separating the IL-4 from the disruptate.

* * * * *